(12) United States Patent
Paolo

(10) Patent No.: US 10,220,168 B2
(45) Date of Patent: Mar. 5, 2019

(54) ELEMENT FOR INHALING MEDICINAL SUBSTANCES

(71) Applicant: HSD Holding Smart Device S.R.L., Rome (IT)

(72) Inventor: Narciso Paolo, Rome (IT)

( * ) Notice: Subject to any disclaimer, the term of this patent is extended or adjusted under 35 U.S.C. 154(b) by 608 days.

(21) Appl. No.: 14/773,001

(22) PCT Filed: Mar. 6, 2014

(86) PCT No.: PCT/IT2014/000067
§ 371 (c)(1),
(2) Date: Sep. 4, 2015

(87) PCT Pub. No.: WO2014/136135
PCT Pub. Date: Sep. 12, 2014

(65) Prior Publication Data
US 2016/0015915 A1 Jan. 21, 2016

(30) Foreign Application Priority Data
Mar. 6, 2013 (IT) .............................. RM2013A0132

(51) Int. Cl.
| A61M 11/06 | (2006.01) |
| A61M 15/00 | (2006.01) |
| A61M 15/08 | (2006.01) |

(52) U.S. Cl.
CPC ............ *A61M 15/08* (2013.01); *A61M 11/06* (2013.01); *A61M 15/0001* (2014.02); *A61M 15/0018* (2014.02); *A61M 15/0016* (2014.02)

(58) Field of Classification Search
CPC ................ A61M 15/08; A61M 15/085; A61M 15/0001–15/0026
See application file for complete search history.

(56) References Cited

U.S. PATENT DOCUMENTS

| 831,004 | A | | 9/1906 | Jousset et al. |
| 2,433,565 | A | | 12/1947 | Korman |
| 3,513,839 | A | | 5/1970 | Vacante |
| 3,747,597 | A | | 7/1973 | Olivera |
| 4,267,831 | A | * | 5/1981 | Aguilar ............... A61M 15/085 128/203.14 |
| 6,478,026 | B1 | * | 11/2002 | Wood ................ A61M 16/0666 128/207.13 |
| 6,679,265 | B2 | * | 1/2004 | Strickland ......... A61M 16/0666 128/207.13 |

(Continued)

OTHER PUBLICATIONS

Notification of Transmittal of the International Search Report and the Written Opinion of the International Searching Authority, or the Declaration, issued in related International Application No. PCT/IT2014/000067 dated Aug. 1, 2014, 9 pages.

(Continued)

*Primary Examiner* — Nyca T Nguyen
(74) *Attorney, Agent, or Firm* — Themis Law

(57) ABSTRACT

An inhaler element, to be inserted inside a nasal cavity for inhaling medicinal substances, includes, inside, a dispensing device providing a convergent conduct for inlet of respiration flow and a divergent conduct for exit of respiration flow, and a storage device for the substance to be inhaled that is in flow communication substantially in correspondence of the transition zone between the convergent conduct and the divergent conduct of the dispensing device.

9 Claims, 3 Drawing Sheets

(56) References Cited

U.S. PATENT DOCUMENTS

| | | | | |
|---|---|---|---|---|
| 8,517,022 | B2* | 8/2013 | Halling | A61M 16/0666 128/206.11 |
| 8,770,199 | B2* | 7/2014 | Flanagan | A61M 16/0672 128/203.12 |
| 2004/0016432 | A1* | 1/2004 | Genger | A61M 16/00 128/204.18 |
| 2005/0211250 | A1* | 9/2005 | Dolezal | A62B 23/06 128/206.11 |
| 2006/0169278 | A1* | 8/2006 | Djupesland | A61M 15/0028 128/200.14 |
| 2006/0266361 | A1* | 11/2006 | Hernandez | A61M 16/06 128/206.11 |
| 2007/0227542 | A1* | 10/2007 | Kashmakov | A62B 23/06 128/206.11 |
| 2007/0283962 | A1* | 12/2007 | Doshi | A62B 23/06 128/206.15 |
| 2008/0221470 | A1* | 9/2008 | Sather | A61B 5/08 600/533 |
| 2009/0308398 | A1* | 12/2009 | Ferdinand | A61M 15/08 128/207.18 |
| 2011/0023869 | A1* | 2/2011 | Djupesland | A61M 15/0028 128/200.14 |

OTHER PUBLICATIONS

Search Report, issued in related Application Serial No. IT RM20130132 on Nov. 6, 2013, 7 pages.

* cited by examiner

Fig. 1

Dispensing Device — 1, 2

Fig. 2

Sec. A-A — 2

Fig. 3

Convergent — 3
Droplets or powder of drug transported by airflow — 6
Nozzle
Drug solution, suspension, solution/suspension or powder — 4
Accelerated airflow — 2

Divergent — Convergent 3

10 — 5

6 — Nozzle arrangement to provent nebulization of expiration phase

9   9   Negative pressure zone   Nebulization

Stem

Fig. 7

ELEMENT FOR INHALING MEDICINAL SUBSTANCES

RELATED APPLICATIONS

This application is a national stage application under 35 U.S.C. § 371 of International Patent Application No. PCT/IT2014/000067, filed on Mar. 6, 2014, which claims the benefit of priority to IT Patent Application No. RM2013A000132, filed Mar. 6, 2013, which applications are incorporated herein by reference in their entireties.

TECHNICAL FIELD

The present invention relates to elements of inhaling medicinal and therapeutic substances.

More specifically, the invention relates to inhaling elements permitting taking medicinal, therapeutic and healing substances and inhaling the same directly within respiratory apparatuses.

BACKGROUND

Inhalation is a technique by which gaseous substances or vapour of volatile substances, or liquid substances or solutions of solid substances finely pulverized are introduced within the respiratory for therapeutical purposes. In fact, inhalations are strongly indicated for treatment of-diseases of upper respiratory, usually acute and chronicle inflammatory processes, by thermal waters (particularly solphorous waters and waters rich of mineral salts), or solutions of medicaments with decongestant, antispasmodic and antiessydativa, expectorant and mucus fludificant action. Furthermore, it represent an important novelty to take vaccines, antibiotics, insulin, or similar molecules, only by taking small amounts.

Known administration or intake of a medicinal substance by the respiratory route can be accomplished in various ways: either by simple inhalation of volatile substances, of fumes released from burning substances or of vapors carrying medicinal substances; or by means of special equipment, also known as inhalers, capable of fragmenting the medicinal preparation into very small particles (mist). In the most common form of inhaler, the medicinal substance emanates for vacuum effect created by a jet of air or of steam passed tangentially to the spout of a capillary tube submerged with the other end within the liquid in which the medicinal substance is dissolved; thereby the liquid is very finely dispersed within the carrier fluid stream.

Said known inhalers however have the disadvantage of being rather bulky, and clearly not all handsets.

It is also known that this type of inhaler can cause significant problems, including phenomena of too much instantaneous delivery, misuse, loss of a large amount of drug, which is deposited on the tongue, within the throat, etc., thus reducing their effectiveness.

Further, disposable portable inhalers are available, allowing one-shot inhalation, for example cortisone to treat asthma, but they consist of immediate supplies that are aggressive for the patient.

SUMMARY

The need to be solved by the solution according to the present invention concerns the possibility of delivering medication through the respiratory tract by means of a device small enough to be inserted into the nostril. Such an administration is advantageous for being able to provide to the body a small amount of drug for long periods, thus improving the absorption and the corresponding health benefit.

Small delivery obtained by the solution according to the invention, allows that the medicinal substance acts maintaining the therapeutically necessary dose, i.e. the right amount that should arrive in a particular district, such as pulmonary alveoli, in order to fully exercise its therapeutic function, thus remaining integrally within the airflow without being absorbed by the body during the run.

Therefore, an object of the present invention is to provide an inhaler device that can be used in any situation, without altering the appearance of the person using it and providing the necessary dose for the specific treatment within a time period that can be set or set in order to obtain a better intake by the body.

A further object of the present invention is to allow a controlled release of the drug in order not to obstruct normal breathing.

It is an object of the present invention to include an inhaler element, to be inserted inside a nasal cavity for inhaling medicinal substances, characterized in that it comprises, inside, a dispensing device, said dispensing device providing a convergent conduit for inlet of respiration flow and a divergent conduct conduit for exit of respiration flow, and storage means for the substance to be inhaled, said storage means being provided in flow communication substantially in correspondence of the transition zone between said convergent conduit and said divergent conduit of said dispensing device.

In particular embodiments, said inhaler element has a substantially frusto-conical shape.

In particular embodiments, said storage means for the substance to be inhaled can be comprised of a reservoir containing the substance and in flow communication with said dispensing device by a joint conduit.

In particular embodiments, said storage means for the substance to be inhaled are comprised of a capillary tube.

Furthermore, according to certain embodiments of the invention, a check valve can be provided at the exit of the divergent conduit of the dispensing device, said valve blocking the flow during the exhalation phase, thus preventing waste of the substance.

Still according to particular embodiments of the invention, a terminal portion of conduit with medicinal substance can be realized so as to have an opening for its exit only on the vertical part facing the divergent conduit.

Furthermore, according to particular embodiments of the invention, flow communication conduit between storage means of the substance to be inhaled and dispensing device can provide a valve having a flexible plate and actuated by negative pressure within the throat of convergent conduit.

In particular embodiments, the openings can be provided on the outer surface of the inhaler device.

Finally, it is an object of the present invention to include an inhaler device characterized in that it comprises two inhaler elements according to each one of the preceding embodiments and a joint element extending between said two inhaler elements.

DESCRIPTION OF DRAWINGS

The invention will be now described, for illustrative but not limitative purposes, with particular reference to the drawings of the enclosed figures, wherein:

FIG. 1 shows a schematic side view of an embodiment of the inhaler element according to the invention;

FIG. 2 shows a front view of the inhaler element according to the invention;

FIG. 3 shows a first embodiment of a dispenser provided in the inhaler element according to the invention;

FIG. 4 shows a second embodiment of a dispenser provided in the inhaler element according to the invention;

FIG. 5 shows a first detail of the inhaler element according to the invention;

FIG. 6 shows a second detail of the inhaler element according to the invention; and FIG. 7 shows a third particular of inhaler element according to the invention.

DETAILED DESCRIPTION

Observing the figures of the accompanying drawings, and initially FIGS. 1 and 2, there is shown an inhaler device 1 according to the invention, in the shape of a truncated hollow cone, made of suitable flexible material which ensures the comfort for the patient and better adherence between the device and the nasal mucosa.

A dispenser device, generally indicated by reference numeral 2, and which will be described in greater detail in the following with reference to the remaining figures, is positioned within the inhaler device 1. The positioning of the dispenser 2 inside the truncated cone shaped inhaler device 1 shown in FIGS. 1 and 2 is merely illustrative, as it can be placed in any position within the same and can be of any size.

Observing now FIG. 3, it is shown in detail a dispensing device 2.

Said dispensing device 2 exploits the difference in air pressure applied by the respiratory act locally to accelerate the speed of the air by means of a convergent duct 3 of any shape, preferably cylindrical shape, localized at any point within the outer dispensing device 2; in the point of maximum speed within the convergent duct 3 it occurs, according to Bernoulli law, a reduction of pressure within the flow drawing the drug in the form of solution, suspension, solution/suspension or powder, dragging the same.

The drug is contained within a tank 4 in fluid communication via a duct 5 with said dispensing device 2, in correspondence of the terminal part of said duct convergent 3.

Downstream of the point of maximum speed, the device may incorporate a divergent conduit 6 of any shape, preferably cylindrical, which will reduce the speed of the air flow and increase the pressure of the same, in such a way as to allow the best integration of the outgoing flow from the device with respiratory airflow.

As already said, in the configuration shown in FIG. 3, the drug, in the form of solution, suspension, solution/suspension or powder to be dispersed within the flow, is contained within a reservoir 4 of any shape and size, in which a conduit 5 is inserted that terminates in the throat of the convergent duct 3; the number of such conduits 5 can be in any number.

Figures 4, 5:
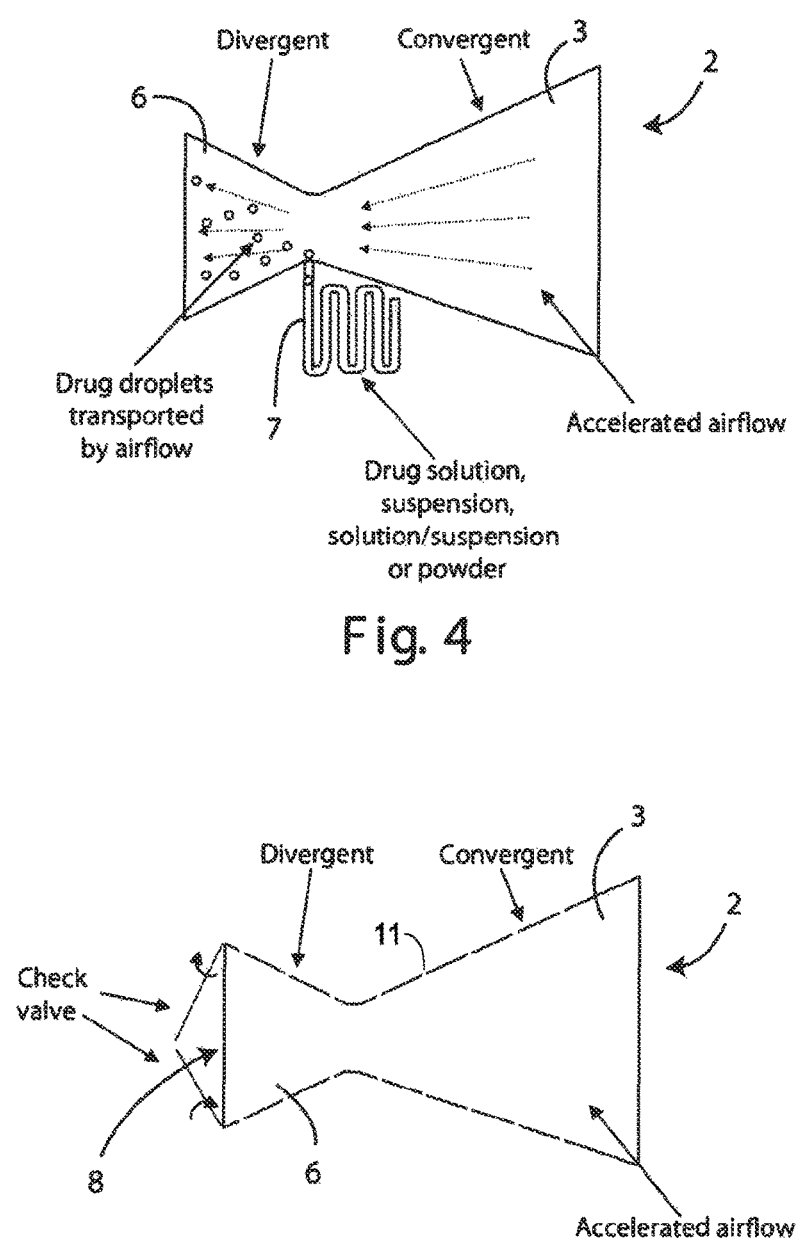

FIG. 4 shows a possible modification of the dispensing device 2, that can be adopted in case the drug is available in the form of solution, suspension, solution/suspension. In this case, the liquid containing the drug is contained within a capillary tube 7 of any shape. Thanks to the water capillarity, when the drug is dragged away by the flow, the liquid moves inside the capillary 7, becoming always available to dragging, remaining faced within the throat of the convergent duct 3; said solution has the advantage of being independent from the vertical tilt.

In a further arrangement shown in FIG. 5, mobile parts 8 can be applied at the exit of the divergent duct 6, allowing the passage of the flow only in the direction towards the lungs, blocking the flow during exhalation, avoiding the dispersion of the drug outwards; these movable parts 8 are applied in FIG. 5 at the end of the divergent duct 6 but can be applied in any point of the dispensing device 2, be in any number and have any shape adapted to give the properties of blocking reverse flow.

In a further arrangement shown in FIG. 6, the elimination of fogging during the exhalation phase is obtained by a particular configuration of the terminal part of the duct 5 afferent the liquid to be atomized, made so as to show an opening 10 for its exit only in the vertical part facing the divergent duct 6.

A further arrangement of the duct 5 is the one shown in FIG. 7, in which said conduit 5 incorporates a valve with a flexible plate 9 actuated by the depression within the throat of the convergent duct 3.

It is also possible that the inhaler device 1 according to the invention provides openings 11 on its outer surface.

They can also be used two devices 1, one in each nostril, which may be connected through a suspender exiting from nostrils.

The dispenser 2 can also occupy the entire volume within the containment truncated cone coinciding with it.

The inhaler element described in the different previous embodiments, once inserted into one or both nostrils of the user exploits the action of compression of air caused by breathing through the lungs, acting as if they were the engine of a common aerosols device, thus allowing the inhalation of particles of medicinal substances which are delivered by the emission of the flow of moist air coming from outside, so as to allow the micro-slow or controlled release of such substances, up to a maximum of eight hours.

Furthermore, the inhaler element according to the invention has the advantage of being a disposable and single-dose device of reduced dimensions so that it can be transported without problems and that will not modify the appearance of the user and to divide the taking of the drug in a fixed time or I a time that can be set for the purpose of having a better intake by the body.

Finally, the device according to the invention also allows the recruitment of vaccines, only possible by means of micro-assumptions as in the present case.

In the foregoing preferred embodiments have been described the modifications of the present invention have been suggested, but it is to be understood that the those skilled in the art can make modifications and changes without departing from the relevant scope, as defined by the claims attached.

The invention claimed is:

1. An inhaler apparatus for insertion inside a nasal cavity for inhaling medicinal substances, the inhaler apparatus comprising:
    a dispensing device having a convergent conduit with a taper and a divergent conduit of opposing taper coupled to the convergent conduit at narrowest points of the convergent and the divergent conduits to define a throat of the dispensing device; and
    a storage container for the medicinal substances to be inhaled, the storage container being in flow communication with the dispensing device to introduce the medical substances at a lateral opening in the throat of the dispensing device.

2. The inhaler apparatus according to claim 1, wherein at least a portion of the dispensing device has a substantially frusto-conical shape.

3. The inhaler apparatus according to claim 1, wherein the storage container for the medicinal substances to be inhaled includes a reservoir containing the medicinal substances and in flow communication with the throat of the dispensing device by a joint conduit.

4. The inhaler apparatus according to claim 1, wherein the storage container for the medicinal substances to be inhaled is comprised of a capillary tube.

5. The inhaler apparatus according to claim 1, further comprising a check valve provided at an exit of the divergent conduit of the dispensing device, the valve configured to block the flow during an exhalation phase, thus preventing waste of the medicinal substances.

6. An inhaler apparatus for insertion inside a nasal cavity for inhaling medicinal substances, the inhaler apparatus comprising:
a dispensing device having a convergent conduit with a taper and a divergent conduit of opposing taper coupled to the convergent conduit at narrowest points of the convergent and the divergent conduits to define a throat of the dispensing device;
a storage container for the medicinal substances to be inhaled, the storage container being in flow communication with the dispensing device to introduce the medical substances at an opening in the throat of the dispensing device; and
wherein a terminal portion of the storage container with the medicinal substances includes the opening only on a vertical part facing the divergent conduit.

7. An inhaler apparatus for insertion inside a nasal cavity for inhaling medicinal substances, the inhaler apparatus comprising:
a dispensing device having a convergent conduit and a divergent conduit of opposing taper coupled to the convergent conduit at narrowest points of the convergent conduit and the divergent conduit to define a throat of the dispensing device; and
a storage container for the medicinal substances to be inhaled, the storage container being in flow communication at the throat of the dispensing device,
wherein flow communication conduit between the storage container of the medicinal substances to be inhaled and the dispensing device includes a valve having a flexible plate configured for actuation by negative pressure within the throat of the convergent conduit.

8. The inhaler apparatus according to claim 1, further comprising openings provided on an outer lateral surface of the inhaler apparatus.

9. The inhaler apparatus according to 1, claim further comprising two dispensing devices and a joint element extending between the two dispensing devices.

* * * * *